United States Patent [19]
Lantzsch et al.

[11] Patent Number: 5,541,332
[45] Date of Patent: Jul. 30, 1996

[54] CHLOROPYRIDINIUM CHLORIDES AND PROCESS FOR THEIR PREPARATION

[75] Inventors: Reinhard Lantzsch, Wuppertal; Klaus Jelich, Overland Park, Kans.; Carl Casser, Köln, Germany; Christoph Mannheims, Leverkusen, Germany; Knud Lawrenz, Köln, Germany

[73] Assignee: Bayer Aktiengesellschaft, Leverkusen, Germany

[21] Appl. No.: 368,179

[22] Filed: Jan. 4, 1995

[30] Foreign Application Priority Data

Jan. 11, 1994 [DE] Germany .......................... 44 00 462.1

[51] Int. Cl.⁶ .................................................. C07D 213/61
[52] U.S. Cl. ............................................................ 546/345
[58] Field of Search ............................................. 546/345

[56] References Cited

FOREIGN PATENT DOCUMENTS 0072777 2/1983 European Pat. Off. .
0546418 6/1993 European Pat. Off. .

OTHER PUBLICATIONS

Chem. Ber. 103 3427–3436 (1970), Rembges.
J. Heterocycle. Chem. vol. 28, pp. 1093–1089 (1991), Park.
J. Chem. Soc. Perkin Trans. I, pp. 1173–1182 (1984), Meth–Cohn.
J. Med. Chem. vol. 33, pp. 1667–1675 (1990), Anderson.
J. Org. Chem., vol. 24, pp. 756–760 (1959).
Schneider, Chemical Abstracts 109:6320, 1988.
Lejeune, Chemical Abstrats 93:95099, 1980.
Lejeune, Chemical Abstracts 93:7972, 1980.

*Primary Examiner*—C. Warren Ivy
*Assistant Examiner*—D. Margaret M. Mach
*Attorney, Agent, or Firm*—Sprung Horn Kramer & Woods

[57] ABSTRACT

A process for the preparation of a chloropyridine of the formula

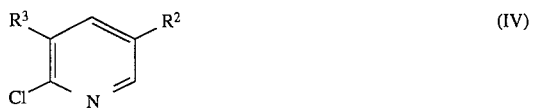

(IV)

which comprises reacting an enamide of the formula

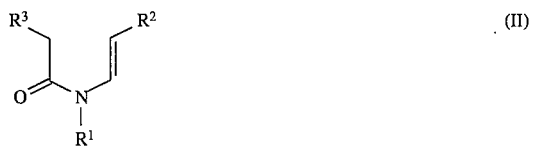

(II)

with a chlorinating agent in the presence of a di-substituted formamide

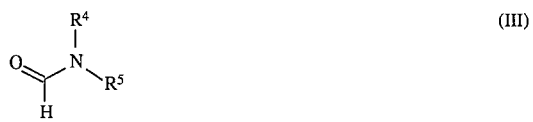

(III)

in which $R^4$ and $R^5$ each individually is alkyl or cycloalkyl or together are alkanediyl, at a temperature between about –30° C. and 100° C., thereby to produce a compound of the formula

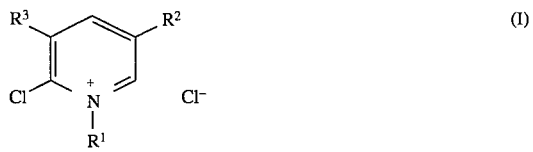

(I)

and subjecting said compound to thermal cleavage.

Compounds I are novel. Compounds IV are known intermediates for agrochemicals and pharmaceuticals.

2 Claims, No Drawings

CHLOROPYRIDINIUM CHLORIDES AND PROCESS FOR THEIR PREPARATION

The invention relates to new chloropyridinium chlorides which can be used as intermediates in the production of agrochemical or pharmaceutical substances, and to a process for their preparation.

It is known that chloropyridinium bromides are obtained by reacting pyridines with benzyl bromides (cf. Chem. Ber. 103 (1970), 3427–3436; J. Heterocyclic Chem. 28 (1991), 1083–1089). However, long reaction times—generally two or more days—are required for this reaction, and the yields are in most cases unsatisfactory.

It is also known that chloropyridinium chlorides can be prepared by reacting N-alkylpyridones with phosphorus (V) chloride (cf. U.S. Pat. No. 3,149,105, Example 3). In this case, however, the products are obtained in unsatisfactory quality and in moderate yield. Moreover, pyridones having the desired substitution pattern can be prepared only with difficulty.

Furthermore, it is known that, by reaction of certain acetenamides with phosphoryl chloride/dimethylformamide, corresponding 5-substituted 2-chloropyridines can be prepared (cf. EP-A 546418).

The present invention relates to
(1) new chloropyridinium chlorides of the general (I)

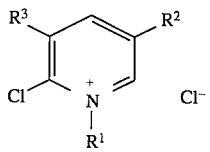

in which
- $R^1$ represents in each case optionally substituted alkyl, alkenyl, alkinyl, cycloalkyl, cycloalkyl-alkyl, arylalkyl or heteroarylalkyl,
- $R^2$ represents optionally substituted alkyl, and
- $R^3$ represents hydrogen, halogen or optionally substituted alkyl (2) a process for the preparation of chloropyridinium chlorides of the general formula (I)

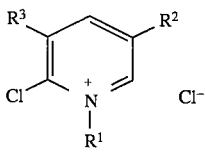

in which
- $R^1$ represents in each case optionally substituted alkyl, alkenyl, alkinyl, cycloalkyl, cycloalkylalkyl, arylalkyl or heteroarylalkyl,
- $R^2$ represents optionally substituted alkyl, and
- $R^3$ represents hydrogen, halogen or optionally substituted alkyl, characterized in that enamides of the general formula (II)

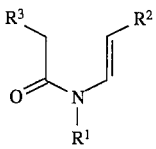

in which
$R^1$, $R^2$ and $R^3$ are as defined above, are reacted with a chlorinating agent in the presence of a formamide derivative of the general formula (III)

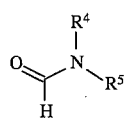

in which
$R^4$ and $R^5$ individually represent alkyl or cycloalkyl or together represent alkanediyl, and optionally in the presence of a diluent at temperatures of between −30° C. and +100° C.

(3) The use of the chloropyridinium chlorides of the formula (I) for the preparation of the chloropyridines of the formula (IV)

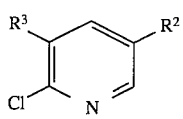

in which
$R^2$ and $R^3$ are as defined above by thermal cleavage.

Surprisingly, the new chloropyridinium chlorides of the formula (I) can be obtained by the process according to the invention in a more simple way and in significantly better yields than by the known methods.

The process according to the invention, in comparison with previously known methods, also proves to be a substantially more cost-effective route to the preparation of chloropyridinium chlorides of the general formula (I) and thus represents a valuable enrichment of the state of the art. Chloropyridinium chlorides of the formula (I) are used to prepare the corresponding chloropyridines.

The process according to the invention is preferably employed to prepare compounds of the formula (I) in which
- $R^1$ represents alkyl having 1 to 6 carbon atoms which is optionally substituted by halogen, (in particular fluorine, chlorine or bromine) or by $C_1$–$C_4$-alkoxy (in particular methoxy or ethoxy), or represents alkenyl or alkinyl each of which has 3 to 6 carbon atoms and is optionally substituted by halogen (in particular fluorine, chlorine or bromine), or represents cycloalkyl or cycloalkyl-alkyl each of which has 3 to 6 carbon atoms in the cycloalkyl moiety and if appropriate 1 to 4 carbon atoms in the alkyl moiety and is optionally substituted by halogen (in particular fluorine, chlorine or bromine) or by $C_1$–$C_4$-alkyl (in particular methyl or ethyl), or represents phenylalkyl, napthylalkyl, pyridylalkyl or thienylalkyl each having 1 to 4 carbon atoms in the alkyl moieties and each optionally substituted by halogen (in particular fluorine, chlorine or bromine), by $C_1$–$C_4$-alkyl (in particular methyl or ethyl) or by $C_1$–$C_4$-alkoxy (in particular methoxy or ethoxy),
- $R^2$ represents alkyl having 1 to 6 carbon atoms which is optionally substituted by halogen (in particular fluorine, chlorine or bromine) or by $C_1$–$C_4$-alkoxy (in particular methoxy or ethoxy), and
- $R^3$ represents hydrogen, halogen (in particular fluorine, chlorine or bromine) or alkyl having 1 to 4 carbon atoms which is optionally substituted by halogen (in particular fluorine or chlorine).

The hydrocarbon radicals mentioned in the definitions of radicals, such as alkyl, alone or in combinations with heteroatoms, such as in alkoxy, are straight-chain or branched even when this is not stated explicitly.

Halogen in general represents fluorine, chlorine, bromine or iodine, preferably fluorine, chlorine or bromine, especially fluorine or chlorine.

The process according to the invention is employed in particular to prepare compounds of the formula (I) in which $R^1$ represents methyl, ethyl, n- or i-propyl, n-, i-, s- or t-butyl, propenyl, butenyl, propinyl or butinyl, or represents benzyl, 1-phenyl-ethyl or 2-phenyl-ethyl in each case optionally substituted by chlorine, methyl, ethyl, n- or i-propyl, or n-, i-, s- or t-butyl, $R_2$ represents methyl, ethyl, n- or i-propyl, or n-, i-, s- or t-butyl each of which is optionally substituted by fluorine, chlorine, bromine, methoxy or ethoxy, and $R^3$ represents hydrogen or chlorine or represents methyl, ethyl, n- or i-propyl, or n-, i-, s- or t-butyl each of which is optionally substituted by fluorine or chlorine.

The definitions of radicals listed above in general, or indicated within preferred ranges, apply both to the end products of the formula (I) and, correspondingly, to the starting materials and/or intermediates which are required in each case for preparation.

These definitions of radicals can be combined with one another as desired, i.e. including combination between the stated ranges of preferred compounds.

Using, for example, N-ethyl-N- (1-propen-1-yl)-acetamide, phosgene and N,N-dimethylformamide as starting materials, the course of reaction in the process according to the invention can be indicated by the following equation:

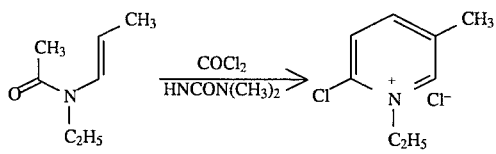

A general definition of the enamides to be used as starting materials in the process according to the invention for the preparation of the compounds of the general formula (I) is given by the formula (II). In the formula (II) $R^1$, $R^2$ and $R^3$ preferably or in particular have those definitions which have already been given above in connection with the description of the new compounds of the formula (I) as being preferred or particularly preferred for $R^1$, $R^2$ and $R^3$.

The starting materials of the general formula (II) are known and/or can be prepared by processes which are known per se (cf. EP-A 546418; J. Chem. Soc. Perkin Trans. I 1984, 1173–1182).

The process according to the invention is carried out using a chlorinating agent. In this context the usual chlorinating agents can be used, for example phosphoryl chloride (phosphorus oxychloride), phosphorus(V) chloride, phosgene, oxalyl chloride, thionyl chloride, perchlorobutanoyl chloride, dichlorodibenzodioxole, N,N-dimethyl-chloromethylimmonium chloride or N,N-diethyl-chloromethylimmonium chloride.

Phosgene is a particularly preferred chlorinating agent in the process according to the invention.

A general definition of the formamide derivatives also to be used in the process according to the invention for the preparation of the compounds of the general formula (I) is given by the formula (III). In the formula (III) $R^4$ and $R^5$, individually, preferably represent alkyl having 1 to 6 carbon atoms or cycloalkyl having 3 to 6 carbon atoms, and especially represent methyl, ethyl, n- or i-propyl, n-, i-, s- or t-butyl, cyclopentyl or cyclohexyl, or together preferably represent alkanediyl having 2 to 6 carbon atoms, especially butane-1,4-diyl or pentane- 1,5-diyl.

Examples of the formamide derivatives of the formula (III) are:

N,N-dimethyl-formamide, N,N-diethyl-formamide, N,N-dipropyl-formamide, N,N-dibutyl-formamide, N-cyclohexyl-N-methyl-formamide and N,N-dicyclohexyl-formamide.

Particularly preferred formamide derivatives are N,N-dimethyl-formamide and N,N-dibutyl-formamide.

The formamide derivatives of the formula (III) are known organic synthesis chemicals.

Suitable diluents for carrying out the process according to the invention are the conventional organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; nitriles such as acetonitrile, propionitrile or butyronitrile; amides such as N,N-dimethylformamide, N,N-dimethylacetamide, N-methylformanilide, N-methylpyrrolidone or hexamethylphosphoric triamide,-sulphoxides such as dimethyl sulphoxide, and sulphones such as tetramethylene sulphone.

Particularly preferred diluents are chlorobenzene and acetonitrile.

When carrying out the process according to the invention the reaction temperatures can be varied within a relatively wide range. It is generally carried out at temperatures of between −30° C. and +100° C., preferably at temperatures of between −10° C. and +75° C., preferably in the initial phase of between −10° C. and +40° C. and subsequently at between +40° C. and +75° C.

The process according to the invention is generally carried out under atmospheric pressure. However, it is also possible to work under increased or reduced pressure, in general at between 0.1 bar and 10 bar.

To carry out the process according to the invention for the preparation of the compounds of the formula (I) requires the use, per tool of enamide of the formula (II), of in general of between 1 and 10 mol, preferably between 1.5 to 5.0 mol, in particular between 2.0 and 3.0 mol, of chlorinating agent and between 1 and 10 mol, preferably between 1.0 and 2.0 mol, of formamide derivative of the formula (III).

When carrying out the process according to the invention, the reaction components can be reacted with one another in any desired sequence.

In a preferred embodiment of the process according to the invention, the formamide derivative of the formula (III) and the chlorinating agent are first placed in a diluent and then the enamide of the formula (II) is metered in at temperatures of between −10° C. and +50° C.; subsequently, further chlorinating agent is metered in. The reaction is then completed by stirring for one or more hours at a somewhat elevated temperature.

The reaction product can be worked up conventionally. It is, for example, diluted with water to from two to three times the volume. The aqueous phase is adjusted to a pH of between 2 and 7 by adding a base, for example sodium hydroxide solution, and then the solvent (water) is carefully distilled off under reduced pressure. The crude product which remains as residue can be purified further in a conventional manner; however, it can also be used as it is for further reactions.

The chloropyridinium chlorides of the formula (I) which can be prepared by the process according to the invention can be used as intermediates in the production of agrochemical or pharmaceutical active substances, or for the preparation of precursors of the latter (cf. the Preparation Examples); for example, thermal cleavage gives the chloropyridines of the formula (IV)

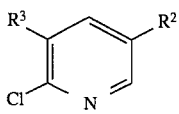

and chlorides of the formula R¹—Cl. Depending on the substituent R¹, different temperature ranges are necessary for the thermolysis, in general between 75° C. and 200° C. The two components can be separated by distillation.

Preparation Examples:

EXAMPLE 1

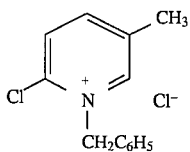

345.4 g (2.2 mol) of N,N-dibutyl-formamide are placed in 800 ml of chlorobenzene. 396 g (4 mol) of phosgene are introduced, the mixture is heated to 40° C., and 388 g (2 mol) of N-benzyl-N-(1-propen-1-yl)-acetamide (content: 97.4%) are added dropwise at an internal temperature of 35° C.–40° C. At an internal temperature of 45° C., a further 99 g (0.5 mol) of phosgene are introduced. The mixture is heated to 70° C. and stirred at 70° C. for 1 hour. Subsequently it is cooled to room temperature (20° C), 500 ml of water are added, and the pH is adjusted to 5 by dropwise addition of about 140 g (1.6 mol) of concentrated sodium hydroxide solution (cooling, internal temperature max. 30° C.). The phases are separated and the aqueous phase is evaporated to dryness at an internal temperature of not more than 50° C. 590 g of a light beige solid are obtained which according to HPLC and ¹H-NMR consists 65% of N-benzyl-2-chloro- 5-methyl-pyridinium chloride=75.5% of theory. By stirring the product with ethyl acetate the pure salt is obtained (m.p. 71° C.–74° C.). ¹H-NMR (D₂O): 2.5 ppm (s; CH₃), 5.9 ppm (s; CH₃), 7.4 and 7.5 ppm (m, C₆, H₅), 8.07 and 8.1 (d, CH), 8.36 and 8.39 (dd, CH), 8.8 (s, CH).

EXAMPLE 2

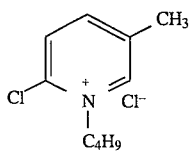

15.5 g (0.1 mol) of N-butyl-N-(1-propen-1-yl)-acetamide and 8 g (0.11 mol) of dimethylformamide are dissolved in 80 ml of dry acetonitrile, and 25.4 g (0.2 mol) of oxalyl chloride are added dropwise with stirring at 15° C. over the course of 30 minutes. The reaction mixture is then heated to 40° C. and a further 12.7 g (0.1 mol) of oxalyl chloride are added dropwise over the course of 15 minutes. The mixture is subsequently stirred at from 40° C. to 45° C. for 10 hours. The acetonitrile is distilled off in vacuo and the remaining oil is stirred into 350 ml of water, adjusted to a pH of 5 using sodium hydroxide solution, and extracted three times with methylene chloride. The aqueous phase is evaporated to dryness in vacuo. The residue consists principally of 2-chloro-5-methyl-N-butyl-pyridinium chloride, which on standing slowly begins to crystallize (m.p. 132° C. to 136° C. (decomp.)). In analogy to Examples 1 and 2, and in correspondence with the general description of the preparation process according to the invention, it is possible—for example—to prepare the compounds of the formula (I) which are listed in Table 1 below.

TABLE 1

Examples of the compounds of the formula (I) to be prepared in accordance with the invention

| Ex. No. | R¹ | R² | R³ | Melting point |
|---|---|---|---|---|
| 3 | —CH₂—⟨C₆H₄⟩—Cl | CH₃ | H | 138–141° C. (decomp.) |
| 4 | —CH₂—⟨C₆H₄⟩—C(CH₃)₃ | CH₃ | H | |
| 5 | —CH₂—CH=CH₂ | CH₃ | H | 151–155° C. (decomp.) |
| 6 | —C₄H₉ | C₂H₅ | H | 132–134° C. (decomp.) |
| 7 | —CH₂—⟨C₆H₅⟩ | CH₃ | Cl | 142–145° C. (decomp.) |
| 8 | CH₃ | CH₃ | H | 80–81° C. |

Examples of the conversion to known intermediates:

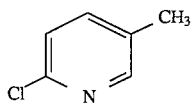

25.4 g (0.1 mol) of N-benzyl-2-chloro-5-methyl-pyridinium chloride are heated in a distillation apparatus at 80° C.–140° C./water pump vacuum. A mixture of 2-chloro-5-methyl-pyridine and benzyl chloride distils over which can be separated by a fine distillation operation. The yield is virtually quantitative.

The decomposition temperature-of N-n-butyl-2-chloro-5-methyl-pyridinium chloride is between 130° C. and 160° C.; that of N-propenyl-2-chloro-5-methyl-pyridinium chloride is between 145° C. and 180° C. The yields of 2-chloro-5-methyl-pyridine are likewise quantitative.

We claim:

1. A chloropyridinium chloride of the formula

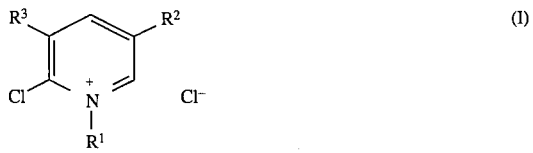

in which
- R¹ is methyl, ethyl, n- or i-propyl, n-, i-, s- or t-butyl, propenyl, butenyl, propinyl or butinyl, or is benzyl, 1-phenyl-ethyl or 2-phenyl-ethyl in each case optionally substituted by chlorine, methyl, ethyl, n- or i-propyl, or n-, i-, s- or t-butyl,
- R² is methyl, ethyl, n- or i-propyl, or n-, i-, s- or t-butyl each of which is optionally substituted by fluorine, chlorine, bromine, methoxy or ethoxy, and
- R³ is hydrogen or chlorine or is methyl, ethyl, n- or i-propyl, or n-, i-, s- or t-butyl each of which is optionally substituted by fluorine or chlorine.

2. A compound according to claim 1, which is N-benzyl-2-chloro-5-methyl-pyridinium chloride of the formula

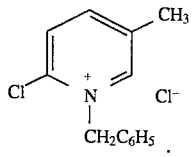

.